US 6,527,893 B1

(12) United States Patent
Boisse et al.

(10) Patent No.: US 6,527,893 B1
(45) Date of Patent: Mar. 4, 2003

(54) METHOD OF MAKING AN ABSORBENT ARTICLE HAVING DOUBLE SIDE CUFFS

(75) Inventors: Sylvie Boisse, Montreal (CA); Thomas J. Helmstetter, Piscataway, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 156 days.

(21) Appl. No.: 09/634,942

(22) Filed: Aug. 8, 2000

Related U.S. Application Data

(62) Division of application No. 09/107,394, filed on Jun. 30, 1998, now Pat. No. 6,171,290.

(51) Int. Cl.$^7$ .......................... A61F 13/15; B32B 31/00
(52) U.S. Cl. ...................... 156/164; 156/163; 156/229; 156/250; 156/289
(58) Field of Search .......................... 156/164, 229, 156/163, 160, 204, 289, 227, 250

(56) References Cited

U.S. PATENT DOCUMENTS

| 4,388,075 A | 6/1983 | Masek et al. |
| 4,490,148 A | 12/1984 | Beckeström |
| 4,695,278 A | 9/1987 | Lawson |

(List continued on next page.)

FOREIGN PATENT DOCUMENTS

| CA | 1242301 | 9/1988 |
| CA | 2021239 | 7/1990 |
| CA | 2126348 | 12/1992 |
| CA | 2109876 | 11/1993 |
| CA | 2149144 | 11/1993 |
| CA | 2175925 | 11/1994 |
| CA | 2190506 | 5/1995 |
| CA | 2211745 | 8/1996 |
| EP | 0329160 A2 | 8/1989 |
| EP | 0534488 A1 | 3/1993 |
| EP | 0876810 A2 | 11/1998 |
| GB | 2296683 A | 8/1996 |
| JP | 8-215242 A * | 8/1996 |
| WO | WO 92/07536 A1 | 5/1992 |
| WO | WO 95/01768 A2 | 1/1995 |
| WO | WO 97/09016 A1 | 3/1997 |

OTHER PUBLICATIONS

EPO Search Report 99111981.9–2314 dated Sep. 25, 2000.

*Primary Examiner*—Jeff H. Aftergut

(57) ABSTRACT

An absorbent article having both outwardly extending and upwardly extending side cuffs is disclosed. The article has a perimeter defined at least in part by a pair of oppositely disposed ends and oppositely disposed sides that extend substantially between the ends. A pair of side flanges extends from a proximal portion adjacent an absorbent structure to a distal portion proximate one of the article sides. Each side flange has a base element, an outer zone disposed adjacent the perimeter and an inner zone disposed between the outer zone and the absorbent structure. There is an elastically extensible element having a width sufficient to span at least the inner zone and a portion of the outer zone, a thickness, and a length. Each elastically extensible element is laminated to the cover material to form a cuff laminate. Each cuff laminate is attached to the base element of the side flange in the outer zone, but each is unattached to the base layer in the inner zone. Finally, the cover is attached to the absorbent structure, at least in a central region of the article. Thus, at least a portion of each cuff laminate is deflected away from the base element of each side flange proximate the inner zone when the elastically extensible element is in a relaxed state.

5 Claims, 4 Drawing Sheets

U.S. PATENT DOCUMENTS

| | | |
|---|---|---|
| 4,704,116 A | 11/1987 | Enloe |
| 4,795,452 A | 1/1989 | Blaney et al. |
| 4,795,454 A | 1/1989 | Dragoo |
| 4,808,177 A | 2/1989 | DesMarais et al. |
| 4,808,178 A | 2/1989 | Aziz et al. |
| 4,900,317 A | 2/1990 | Buell |
| 4,938,754 A | 7/1990 | Mesek |
| 5,032,121 A * | 7/1991 | Mokry ........................ 604/366 |
| 5,074,856 A * | 12/1991 | Coe et al. .................... 604/370 |
| 5,085,654 A | 2/1992 | Buell |
| 5,234,422 A | 8/1993 | Sneller et al. |
| 5,308,346 A | 5/1994 | Sneller et al. |
| 5,346,486 A | 9/1994 | Osborne, III et al |
| 5,387,210 A | 2/1995 | Murakami |
| 5,413,569 A | 5/1995 | Yamamoto |
| 5,447,507 A | 9/1995 | Yamamoto |
| 5,542,941 A | 8/1996 | Morita |
| 5,567,260 A * | 10/1996 | McFall ........................ 156/201 |
| 5,620,431 A | 4/1997 | LeMahieu et al. |
| 5,624,426 A | 4/1997 | Roe et al. |
| 5,591,147 A | 7/1997 | Couture-Dorschner et al. |
| 5,681,303 A | 10/1997 | Mills et al. |
| 5,704,928 A | 1/1998 | Morita et al. |
| 5,730,738 A | 3/1998 | McFall et al. |
| 5,895,382 A | 4/1999 | Popp et al. |
| 5,899,894 A | 5/1999 | Palumbo et al. |
| 6,231,554 B1 * | 5/2001 | Menard ................ 604/385.01 |

\* cited by examiner

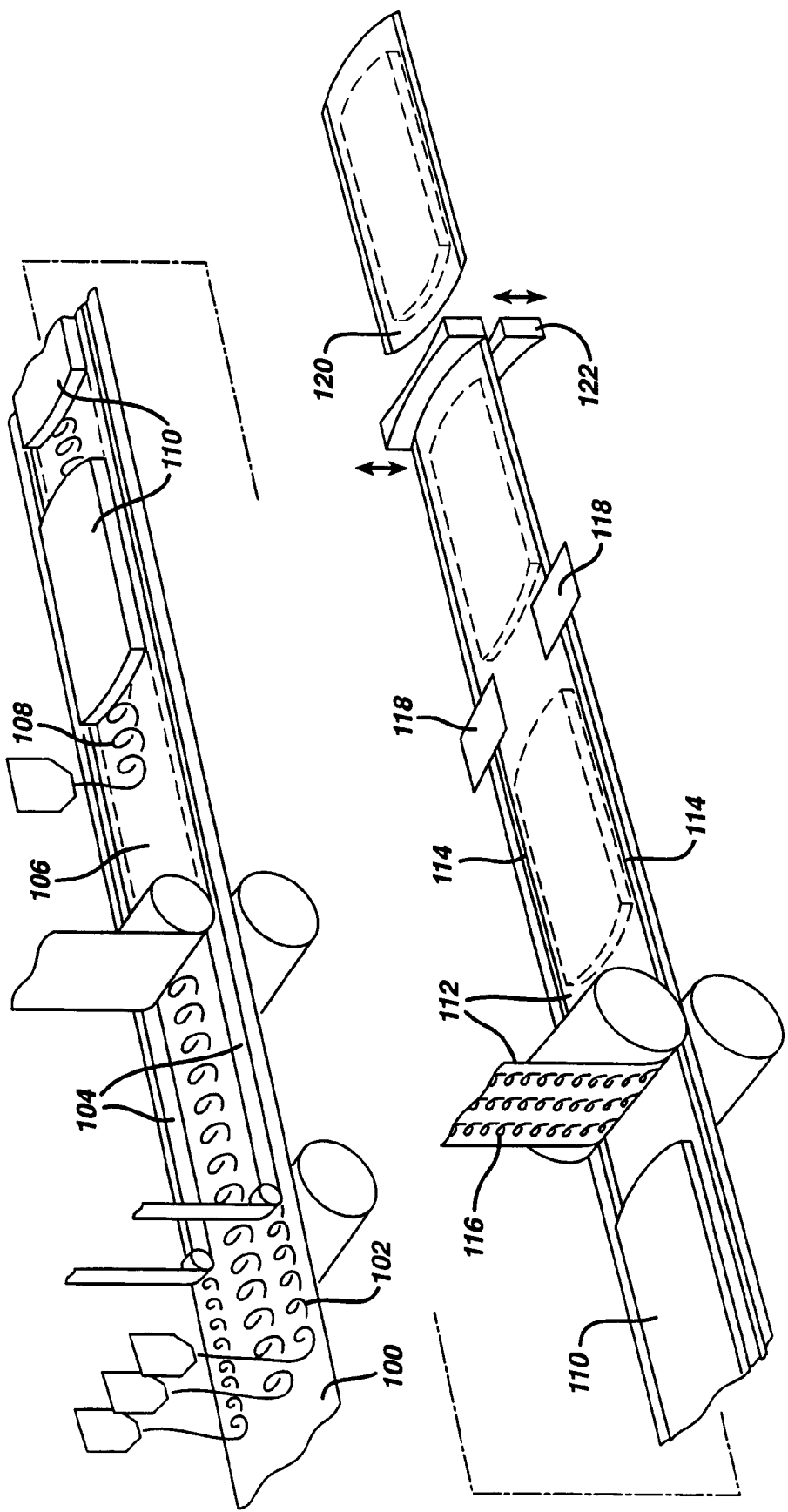

METHOD OF MAKING AN ABSORBENT ARTICLE HAVING DOUBLE SIDE CUFFS

This is a Divisional of prior application Ser. No. 09/107,394, filed Jun. 30, 1998, now U.S. Pat. No. 6,171,290.

FIELD OF THE INVENTION

The present invention relates to absorbent articles having side cuffs to reduce side leakage, more particularly to absorbent articles having both outwardly extending and upwardly extending side cuffs.

BACKGROUND OF THE INVENTION

Developers continually try to improve the fluid containment and comfort of absorbent articles, such as diapers, incontinence guards, and santionary napkins. They have addressed side leakage problems by the addition of flexible, often elasticized, outwardly-extending, leg cuffs such as disclosed in Mesek et al., U.S. Pat. No. 4,388,075, Mesek U.S. Pat. No. 4,938,754, and Menard et al., EP 0 534 488.

Later, product developers added upwardly extending "barrier cuffs" near the side edge of the absorbent structure in the absorbent articles. Examples of these barrier cuffs can be seen in Enloe, U.S. Pat. No. 4,695,278, Lawson, U.S. Pat. No. 4,695,278, Buell, U.S. Pat. No. 4,900,317, and LeMahieu et al., U.S. Pat. No. 5,620,431. These barrier cuffs are often added as separate pieces that must be handled and attached to the absorbent article. These cuffs also include individual or multiple elastic strands or ribbons, and they apply the contracting forces in discrete, spaced, regions.

What is needed is a novel absorbent article having both an outwardly extending side flange and an upwardly extending barrier cuff that is comfortable to the user and that is easily manufactured in a continuous, commercial manufacturing process.

SUMMARY OF THE INVENTION

An absorbent article having both outwardly extending and upwardly extending side cuffs is disclosed. The article has a perimeter defined at least in part by a pair of oppositely disposed ends and oppositely disposed sides that extend substantially between the ends. The article has a liquid permeable cover material, a liquid repellent barrier material attached to the cover material proximate the perimeter, and an absorbent structure disposed between the cover material and the barrier material. A pair of side flanges extends from a proximal portion adjacent the absorbent structure to a distal portion proximate one of the article sides. Each side flange has a base element, an outer zone disposed adjacent the perimeter and an inner zone disposed between the outer zone and the absorbent structure. There is an elastically extensible element having a width sufficient to span at least the inner zone and a portion of the outer zone, a thickness, and a length.

Each element is connected to each side flange, and the length of the elastically extensible element is substantially greater than its width, which in turn is substantially greater than its thickness. Each elastically extensible element is laminated to the cover material to form a cuff laminate. Each cuff laminate is attached to the base element of the side flange in the outer zone, but each is unattached to the base layer in the inner zone. Finally, the cover is attached to the absorbent structure, at least in a central region of the article. This permits at least a portion of each cuff laminate to be deflected away from the base element of each side flange proximate the inner zone when the elastically extensible element is in a relaxed state. The invention also relates to a process for forming such an article.

BRIEF DESCRIPTION OF THE DRAWING

FIG. 7 illustrates a schematic diagram of the method of forming an absorbent article according to the present invention.

DETAILED DESCRIPTION OF THE PREFERRED EMBODIMENT

Figure 1:
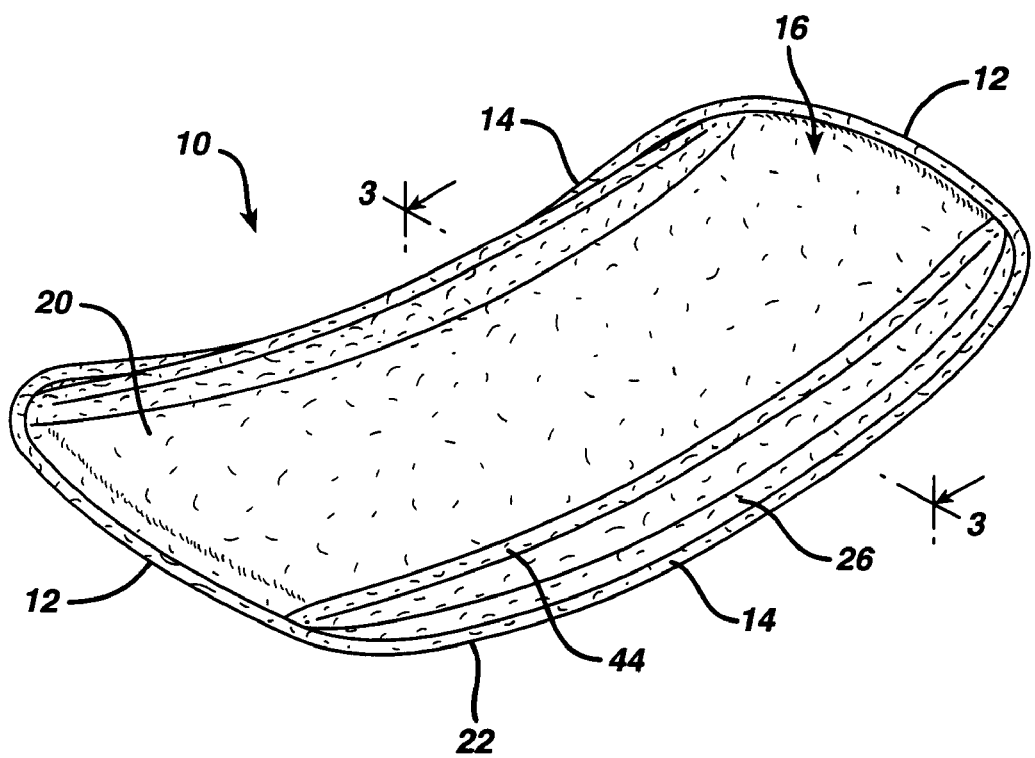
FIG. 1 shows a perspective view of an absorbent article according to the present invention.
Figure 2:
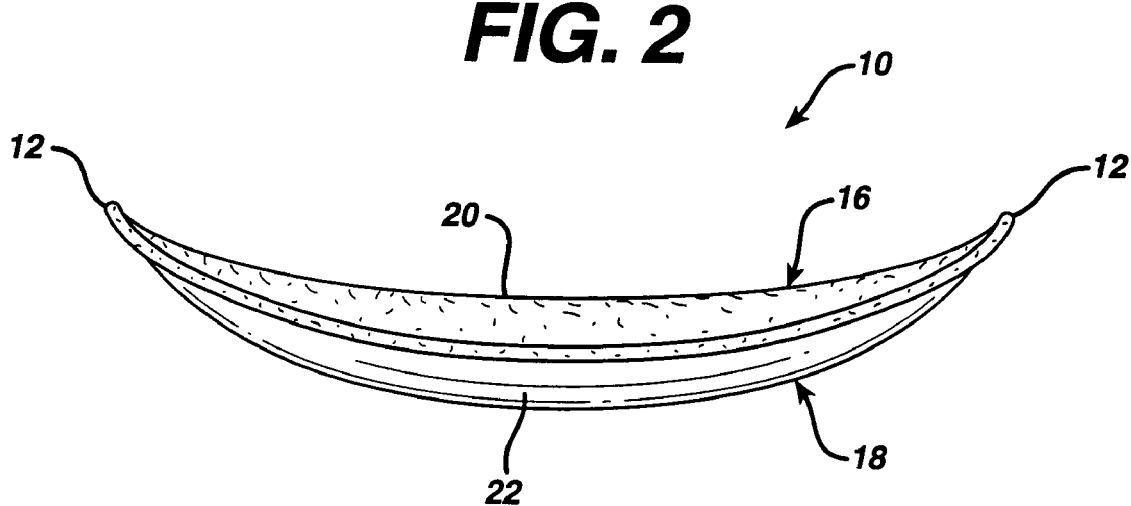
FIG. 2 shows a side elevation of the absorbent article of FIG. 1.
Figure 3:
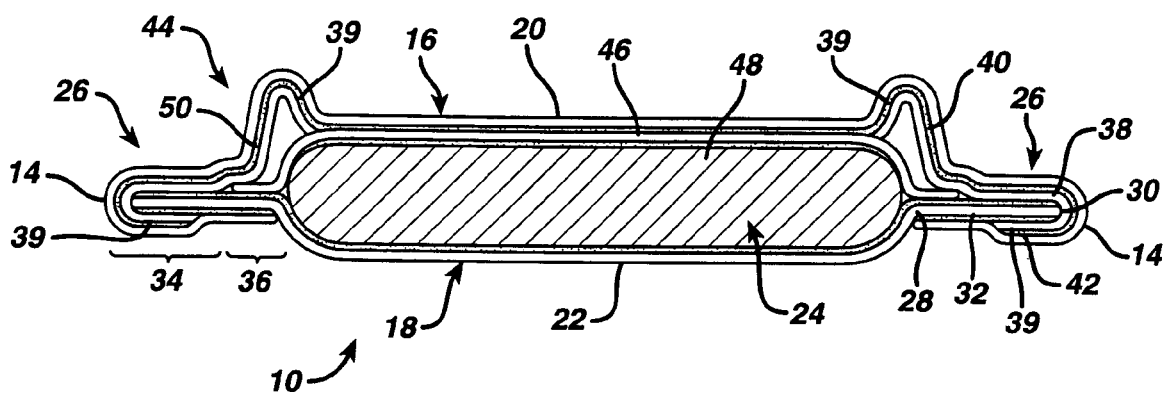
FIG. 3 shows a cross-section along line 3—3 of FIG. 1.

Referring to FIGS. 1–3, an absorbent article 10 having a perimeter defined at least in part by a pair of oppositely disposed ends 12 and oppositely disposed sides 14 that extend substantially between the ends 12.

The article 10 has a body facing surface 16 and a garment facing surface 18. The article 10 has a liquid permeable cover 20 and a liquid impermeable barrier 22.

The cover 20 and the barrier 22 are attached proximate the perimeter of the article 10. An absorbent structure 24 is disposed between the cover 20 and the barrier 22.

A side flange 26 extends outwardly along each side 14 of the article 10. Each side flange 26 extends outwardly from a proximal portion 28 adjacent the absorbent structure 24 to a distal portion 30. Each side flange 26 has a base element 32, an outer zone 34 disposed adjacent the perimeter of the article 10 and an inner zone 36 disposed between the outer zone 34 and the absorbent structure 24.

An elastically extensible element 38 is operatively connected to each side flange 26. The elastically extensible element 38 is formed into a cuff laminate 39 with the cover 20, at least proximate the sides 14. Preferably, a first surface 40 of the elastically extensible element 38 is laminated to the cover 20 to form this cuff laminate 39. The cuff laminate 39 is attached to the base element 32 in the outer zone 34, but it is not directly attached to the base element 32 in the inner zone 36. Preferably, a second surface 42, opposite the first surface 40, forms the exposed portion of the cuff laminate 39 that is attached to the base element 32 in the outer zone 34. Therefore, at least a portion of the cuff laminate 39 is deflected away from the base element 32 of each side flange 26 proximate the inner zone 36 to form an upwardly extending barrier cuff 44.

The cover 20 is a liquid permeable element, and it is useful to contain the absorbent structure 24, permit bodily exudates to pass into the absorbent structure 24, at least partially to mask absorbed bodily exudates, and to provide a comfortable body facing surface 16. The cover 20 may be of any structure that is sufficiently flexible to flex with the absorbent article 10 and that is capable of allowing bodily fluids to pass therethrough while substantially containing any potentially mobile components of the absorbent structure 24. A representative, non-limiting list of useful structures includes woven fabrics, nonwoven fabrics, apertured or perforated films, porous foams (including perforated foams), sintered plastics, and the like. A representative, non-limiting list of materials useful in forming such structures includes cellulosics, such as cotton, rayon, wood fluff pulp, and the like; hydrocarbon synthetics, such as polyolefins, polyesters, polyurethanes, polyamides, polytetrafluoroethylene ("PTFE"), and the like; silicones, such as polysiloxanes and the like; bonding agents; wetting agents, such as surfactants; and any other materials which are useful as absorbent article components. One or more of these materials may be included in a laminated structure to form the cover 20.

Preferably, the cover 20 is formed from a sheet of flexible material that has a basis weight of less than about 60g/m² ("gsm"), a more preferred basis weight is between about 10 and about 60 gsm, and a most preferred basis weight is between about 15 and about 35 gsm.

The barrier 22 is a preferably a liquid impermeable element, and it is useful to contain the absorbent structure 24, prevent bodily exudates from passing out of the absorbent structure 24 to the user's garments or otherwise, and to provide a comfortable garment facing surface 18. The barrier 22 may be of any structure that is sufficiently flexible to flex with the absorbent article 10 and that is capable of preventing bodily fluids from passing therethrough and also substantially containing any potentially mobile components of the absorbent structure 24. A representative, non-limiting list of useful structures includes fabrics, such as nonwoven and woven fabrics; films, including apertured, perforated, or microporous films; foams, such as porous or nonporous, closed cell foams; sintered plastics, and the like. A representative, non-limiting list of materials useful in forming such structures includes cellulosics, such as cotton, rayon, wood fluff pulp (including paper and coated or otherwise laminated paper), and the like; hydrocarbon synthetics, such as polyolefins, polyesters, polyurethanes, polyamides, PTFE, and the like; silicones, such as polysiloxanes and the like; bonding agents, repellents, and other material treatments; and any other materials which are useful as absorbent article components. One or more of these materials may be included in a laminated structure to form the barrier 22.

Preferably, the barrier 22 is formed from a sheet of flexible material that has a thickness of less than about 2 mm. More preferably the barrier is formed from a film having a thickness of less than about 0.1 mm, and most preferably between about 0.01 and about 0.05 mm.

Figure 4:
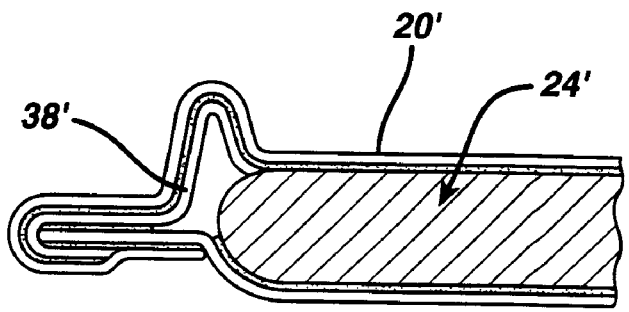
FIGS. 4–6 show partial views of the cross-section of FIG. 3 of three alternative embodiments.
Figure 5:
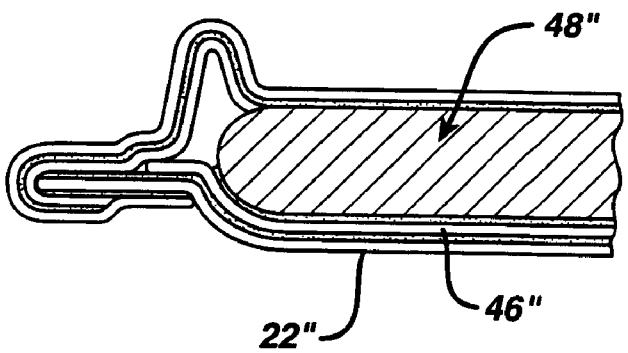

The absorbent structure 24 is used to acquire and to retain exuded bodily fluids. The absorbent structure 24 may be a single, substantially uniform structure, or it may be a more complex, layered or otherwise asymmetrical structure. In a preferred embodiment, the absorbent structure 24 comprises at least one intermediate layer 46 and at least one retention element 48. The intermediate layer(s) 46 may be arranged and configured to acquire, distribute, temporarily hold, and/or mask bodily exudates and to help to stabilize the whole absorbent structure 24, while the retention element will generally take up such bodily exudates from the intermediate layer(s). In a particularly preferred embodiment as shown in FIG. 3, a first intermediate layer is disposed between the retention element 48 and the cover 20, is wider than the retention element 48, and extends at least into the inner zone 36 of the side flange 26. Again, this helps to stabilize the retention element 48. In another embodiment shown in FIG. 4, the absorbent structure 24' is a single layer. In yet another embodiment shown in FIG. 5, an intermediate layer 46" is disposed between the retention element 48" and the barrier 22". This intermediate layer 46" may be used as a wicking layer or stabilizing element.

The absorbent structure 24 and/or the individual layers (intermediate layer(s) 46 and/or retention element 48) may be of any structure that is sufficiently absorbent of bodily fluids to function as a sanitary napkin, incontinence device, diaper, or similar product. A representative, non-limiting list of useful structures includes woven fabrics, nonwoven fabrics (including fibrous batts, tissues, and the like), apertured or perforated films, porous foams, sintered plastics, and the like. Such structures may also include conventional absorbent materials and high absorbency materials such as superabsorbent foams, particles, fibers, films, sheets, and the like. A representative, non-limiting list of materials useful in forming such structures includes cellulosics, such as cotton, rayon, wood fluff pulp, sphagnum, and the like; hydrocarbon synthetics, such as polyolefins, polyesters, polyurethanes, polyamides, PTFE, and the like; superabsorbent materials, such as hydrolyzed, cross-linked polyacrylates, polyacrylonitriles, acrylics, grafted polymers, and the like; odor-control agents, such as fragrances, zeolites, sequesterants, and the like, and any other materials which may be useful as absorbent article components.

The length of the elastically extensible element 38 is substantially greater than its width, and the width is substantially greater than the thickness of the extensible element 38. The elastically extensible element 38 may be of any elastically extensible structure that is elastic to impart a raised cuff and longitudinal curve to the article 10. A representative, non-limiting list of useful structures includes sheets, films, foams, ribbons, woven or nonwoven webs, and the like. A representative, non-limiting list of materials useful in forming such structures includes hydrocarbon synthetics, such as polyolefins, polyesters, polyurethanes, polyamides, PTFE, block copolymers (such as styrene-butadiene-styrene and styrene-isoprenestyrene copolymers), ethylene-vinyl acetate copolymers, synthetic rubber, and the like; silicones, such as polysiloxanes and the like; natural rubber; and any other materials which are useful as absorbent article components.

The properties of the elastically extensible element 38 are balanced with the properties of the rest of the materials used to fabricate the absorbent article 10. This allows the elastically extensible element 38 to curve the article 10 in the longitudinal direction, and to form barrier cuffs 44 along the article's side edges 14. Preferably, the elastically extensible element 38 is formed from a sheet of elastomeric material having a tensile strength of less than 200 psi, more preferably, from about 10 to 100 psi, and most preferably, from about 25 to about 50 psi. Additionally, it is preferred that the elastomeric material has an elongation to break of at least about 100%, more preferably, from about 200% to about 350%, and most preferably, from about 250% to about 300%. These materials can be tested according to ASTM D-3574-95. It is also preferred that the recovery of the material be at least about 60%, more preferably, at least about 80%, and most preferably, at least about 90%.

While we do not wish to be held to this theory, it is believed that a sheet of elastomeric material or a similar geometry has unique properties that allow the present invention to be achieved. First, upon elongation under tension, both the thickness and width of the material decrease. When portions of the material are then secured in the tensioned condition and the tension is subsequently released, it is believed that the material will attempt to regain at least some of both its thickness and its width. Thus, the material buckles and separates from the base element 32 to form the upstanding barrier cuff 44. In order to optimize this, the width of the elastically extensible element 38, the inner zone 36 and the outer zone 34 are balanced to provide the upstanding barrier cuff 44. If there is insufficient width to the inner zone 36, there will be very little if any barrier cuff 44. Conversely, if there is insufficient width in the outer zone 34, the side cuff will be substantially eliminated.

As discussed above, a cuff laminate 39 is formed comprising the first surface 40 of the elastically extensible element 38 and the cover 20. The elastically extensible element 38 is preferably combined in this cuff laminate 39 in an extended state. The cuff laminate 39 is attached to the base element 32 in the outer zone 34 of the side flange 26, but it is not directly attached to the base element 32 in the inner zone 36. Thus, the cuff laminate is able to separate from the base element 32 inwards of the outer zone 34 to form the upwardly extending barrier cuff 44 as the elastically extensible element 38 reverts to a relaxed state.

The material used for the base element 32 may be the similar to the material used for the cover 20 and/or the barrier 22, as described above. The base element 32 itself may be a separately attached element, but it is preferred that the base element 32 is a continuation of the barrier 22 as shown in FIG. 3. In this embodiment, it can be seen that the side flange 26 is formed of the materials of construction of the rest of the absorbent article 10, and no additional structure need be manipulated and attached to the product to form both the outwardly extending side flange 26 and the upwardly extending barrier cuff 44.

Figure 6:
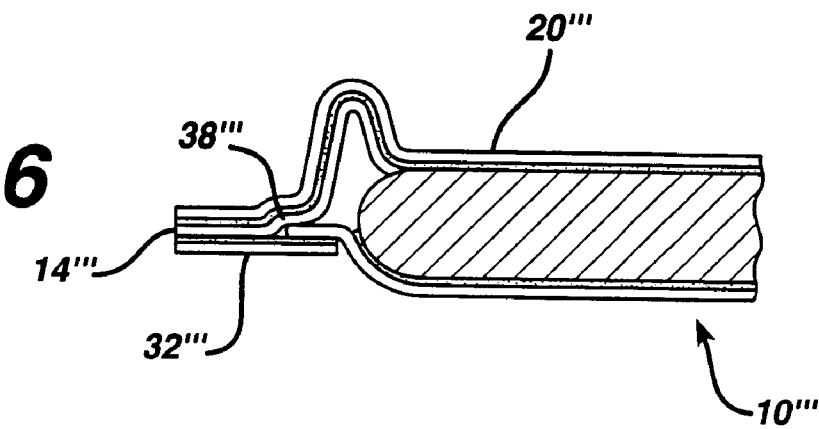

Of course, if the base element 32''' is formed of a separate element, this separate element could be attached to the rest of the absorbent article 10 as shown in FIG. 6. In this embodiment, both the cover 20''' and the elastically extensible element 38''' extend only to the side edge 14''' of the article 10'''. The attachment may be adhesive, ultrasonic, sewn, or other attachment mechanisms that will be known to those of ordinary skill in the art.

The separation of the cuff laminate 39 and the base element 32 in the inner zone 36 may be achieved by several methods. If the two elements are adhesively attached, the separation may be achieved by: (1) preventing the application of adhesive material between the elements in the inner zone 36; (2) detackifying any adhesive material present in the inner zone 36; (3) masking such adhesive; or (4) other methods as recognized by those skilled in the art. If the elements are attached through heat and/or pressure, the separation may be achieved by: (1) maintaining the inner zone at a temperature and/or pressure below that necessary for bonding; (2) maintaining a separation between the elements in the inner zone 36 during the attachment of the elements; or (3) other methods recognized by those skilled in the art. Further attachment methods and related separation methods will also be recognized by those skilled in the art.

The absorbent article 10 may be made by hand, or it may be manufactured according to a process such as is outlined in FIG. 7 and described below. First, the cover material 100, is unwound from a supply roll. A first laminating adhesive material 102 is applied to a surface of the cover material 100, and elastically extensible material 104 is stretched and adhered to the cover material 100. This forms a cuff laminate in one or more regions of the cover material 100. Preferably, the elastically extensible material 104 is stretched at least about 10% prior to being adhered to the cover material. More preferably, it is stretched from about 10% to about 40%, and most preferably, it is stretched from about 15% to about 30%.

An intermediate layer 106 may then be adhered to the cover material 100 in a manner to overlap the elastically extensible material 104. It is this overlap that can prevent the later lamination of the cuff laminate and the base element.

After the intermediate layer 106 has been adhered to the cover material 100, a second adhesive material 108 can be applied to the construction. This second adhesive material 108 may cover at least a portion of the intermediate layer 106. A retention element 110 can then be placed on the construction and adhered to the intermediate layer 106.

Finally, a barrier material 112 is applied to the construction. The barrier material 112 is preferably narrower than the cover material 100 to allow the extreme edges of the cuff laminate to be wrapped around the side edges 114 of the barrier material 112 and secured on the exposed surface of the barrier material 112, e.g., at a folding station 118. The barrier material 112 may have disposed thereon a construction adhesive 116. Individual absorbent articles 120 may be formed from the resulting construction proximate the longitudinal ends of the absorbent structure 110, e.g., with a reciprocating cutter 122 or a rotary cutter (not shown). Attachment adhesive protected by a release liner may then be applied to a portion of the remaining exposed regions of the barrier material 112. The resulting products can then be packaged and stored until use.

In an alternative embodiment in which the intermediate layer is positioned between the retention element 110 and the barrier material 112, the process may be modified slightly. The retention element 110 would be placed onto the second adhesive material 108 between the elastically extensible (may overlap slightly the elastic) material 104. Laminating adhesive 116 again may be applied on the barrier material 112. An intermediate layer, wider than the retention element, would be applied to the barrier. Another layer of laminating adhesive can be applied in the middle of this intermediate layer to insure good bonding of the retention element. This construction is then joined to the cover/elastic/retention layer. The portion of the intermediate layer that is wider than the retention element deactivate the adhesive thereby creating the raised region 44.

In a second alternative method of fabrication in which the intermediate layer is eliminated, the process would again be modified. In particular, the retention element 110 is placed on the second adhesive material 108 between the elastically extensible (may overlap slightly the elastic) material 104. However, this second adhesive material 108 is applied such that there are two regions without applied adhesive on both sides of the retention element 110. The process continues as described above with the application of the barrier material 112 to the retention element 110 and cover/elastic construction. Again, the barrier material 112 should be free of adhesive in a region that corresponds to the uncoated portion of the cover. These uncoated portions of the cover material 100 and barrier material 112 prevent the attachment of these elements in the inner zone to create the barrier cuff 44.

In use, the product may be removed from its packaging, and, e.g., attached in the crotch portion of a user's undergarment after the attachment adhesive is exposed. When so attached, the elastically extensible element 38 can relax to impart a curve along the longitudinal axis of the product, and to urge the cuff laminate 39 away from the base element 32 to form upwardly extending barrier cuffs 44 to help to prevent bodily exudates from leaking around the longitudinal sides 14 of the article 10.

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of forming an absorbent article comprising the steps of:
   a) elongating a first elastically extensible material and attaching it to a substantially continuous length of a cover material to form a first cuff laminate proximate a first side margin of the cover material;
   b) attaching a discrete length of an absorbent structure having longitudinal ends and lateral sides adjacent the elastically extensible material, leaving the elastically extensible material substantially uncovered by the absorbent structure;
   c) attaching a substantially continuous length of a barrier material to the absorbent structure, to a portion of the cover material adjacent the longitudinal ends of the absorbent structure, and to a portion of the cuff laminate proximate the side margin of the cover material, leaving a portion of the cuff laminate in an inner zone, between the side margin of the cuff material and a side margin of the absorbent structure, substantially unattached to the barrier material; and
   d) separating an absorbent article from the continuous length of the cover material.

2. The method of claim 1 further comprising the step of elongating a second elastically extensible material and attaching it to the substantially continuous length of the cover material to form a second cuff laminate proximate a second side margin, opposite the first, of the cover material.

3. The method of claim 2 further comprising the step of attaching an intermediate layer to the cover material between the first and second elastically extensible materials.

4. The method of claim 1 further comprising the step of attaching an intermediate layer to the barrier material.

5. The method of claim 1 further comprising the step of applying an adhesive material to the cover material, the first and second elastically extensible materials, and the barrier material in at least one pattern to avoid attachment of all of the cover material, at least one of the elastically extensible materials and the barrier material in the inner zone.

\* \* \* \* \*